United States Patent [19]
Ochiai et al.

[11] Patent Number: 6,049,731
[45] Date of Patent: Apr. 11, 2000

[54] PATIENT MONITORING APPARATUS

[75] Inventors: Ryoichi Ochiai; Yoshihiro Sugo; Takeshi Sohma; Rie Tanaka; Wenxi Chen, all of Tokyo, Japan

[73] Assignee: Nihon Kohden Corporation, Tokyo, Japan

[21] Appl. No.: 09/136,964

[22] Filed: Aug. 20, 1998

[30] Foreign Application Priority Data

Aug. 20, 1997 [JP] Japan .................................. 9-223271

[51] Int. Cl.$^7$ .................................................. A61B 5/022
[52] U.S. Cl. .......................................................... 600/513
[58] Field of Search .................................. 600/485, 495, 600/510, 513

[56] References Cited

FOREIGN PATENT DOCUMENTS 0 123 313  10/1984  European Pat. Off. .......... A61B 5/02
0 542 413   5/1993  European Pat. Off. ...... A61B 5/0432
26 04 460   8/1977  Germany .......................... A61B 5/04

*Primary Examiner*—William E. Kamm
*Attorney, Agent, or Firm*—Sughrue, Mion, Zinn, Macpeak & Seas, PLLC

[57] ABSTRACT

A pacing-pulse detecting circuit 3 detects pacing pulses from an electrocardiogram signal led from an electrocardiogram electrode 1. A mode-status judging means 21 judges a mode status, a pacing mode or a nonpacing mode, on the basis of the pacing pulse detected. The detect result is transmitted to a CPU 5. The CPU causes a display device 10 to display the result. An operator sees the display and operates a key 22, and gives an instruction to start a blood pressure measurement to the CPU 5. The CPU 5 drives a pump 13 and an exhaust valve 14 to supply and discharge air to and from a cuff 11, and measures a blood pressure by use of pressure data led from a pressure sensor 15.

1 Claim, 17 Drawing Sheets

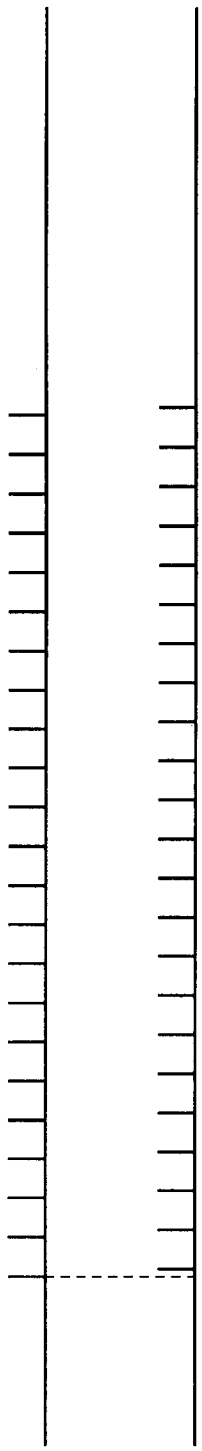
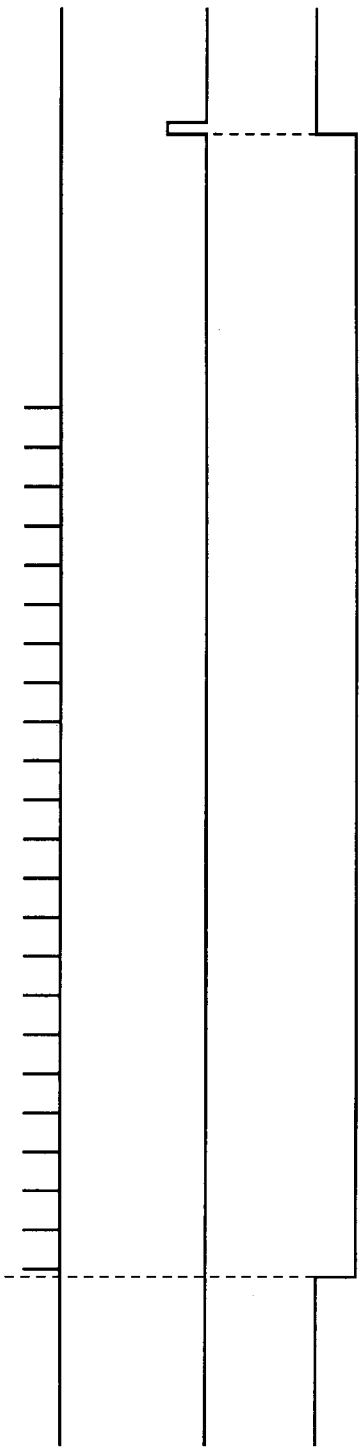
FIG. 4A
FIG. 4B
FIG. 4C
FIG. 4D
FIG. 4E
FIG. 4F

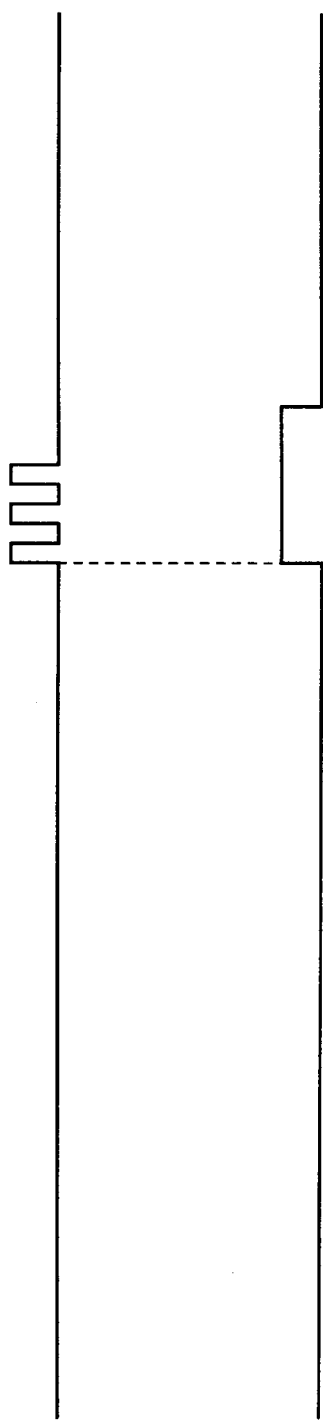
FIG. 14A
FIG. 14X
FIG. 14Y

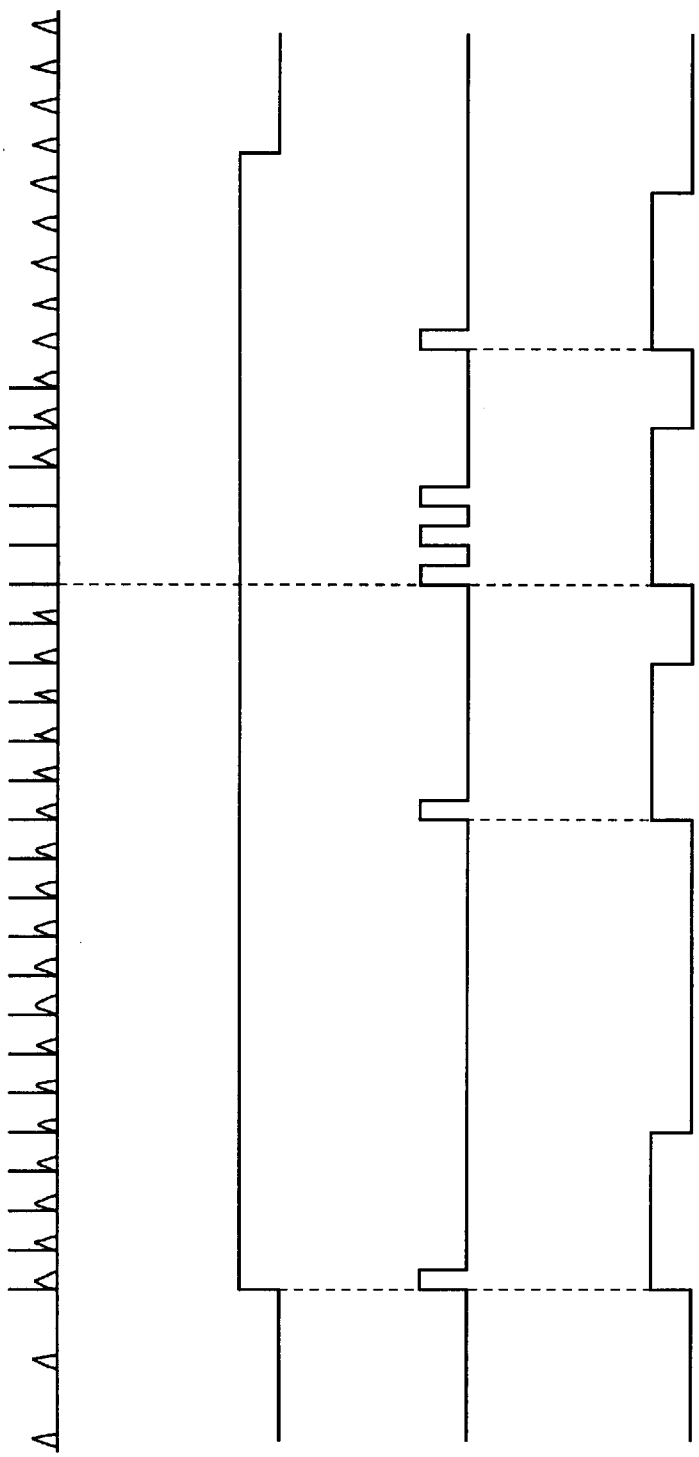

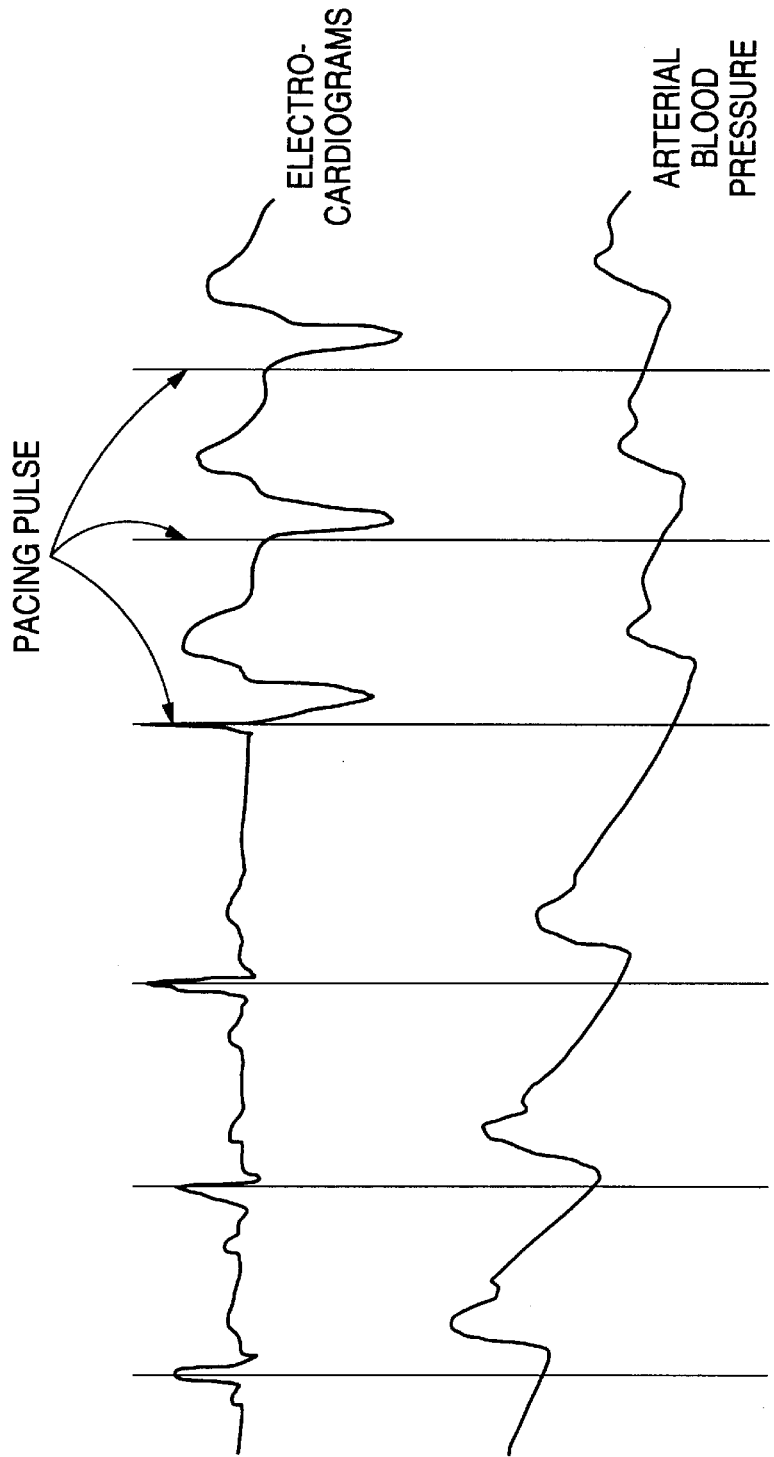

PATIENT MONITORING APPARATUS

BACKGROUND OF THE INVENTION

1. Field of the Invention

The present invention relates to an apparatus for non-invasively monitoring at least electrocardiograms and blood pressures, the electrocardiograms being led from an electrocardiogram electrode and the blood pressure being output from a non-invasive blood-pressure measuring apparatus (NIBP).

2. Related Art

The non-invasive patient monitoring apparatus monitors mainly electrocardiograms, arterial oxygen saturation and blood pressure (measured by the NIBP) as parameters representing dynamic states of circulation of a patient. The patient monitoring apparatus periodically measures a blood pressure by the NIBP. When the blood pressure abruptly changes during the interval between the adjacent measurements, the patient monitoring apparatus will miss the measurement of the abrupt change of blood pressure. To avoid the missing of the measurement, the heart rate, which is relatively sensitive to changes in the status of cardiovascular circulation, is used for its parameter monitoring. If the heart rate being monitored varies out of a preset range of its values, the patient monitoring apparatus generates an alarm. The operator recognizes the generated alarm and operates the non-invasive blood-pressure measuring apparatus to measure a blood pressure of the patient.

In a case where a patient suffering from a sinus arrhythmia at an acute stage, and an external or implantable pacemaker is attached to him in the ICU, ward or operating room, it is necessary to carefully monitor his blood pressure because the following situations will take place.

(1) When the ventricle is paced by use of a pacemaker, the cardiac output sometimes decreases even if at the same heart rate. This fact is known. When the ventricle of the heart is paced, and a dynamic state of the heart shifts from a sinus rhythm contraction (which is attendant with an autonomic contraction of the atrium) to a ventricular contraction, the heart exhibits an electrocardiogram as shown in FIG. 16(a). In this case, the cardiac output decreases to about 80% of that in a normal state, and the blood pressure also decreases as shown in FIG. 16(b).

(2) There is a case where when the patient is paced for a long time, a stimulus threshold value of the myocardium abnormally increases, and the same phenomenon likewise takes place depending on some kinds of medicines prescribed. In this case, the pacing is imcompetence in spite of pacing to recover from the bradycardia, as shown in FIG. 17(a). At this time, it is estimated that a blood pressure of the arteria decreases as shown in FIG. 17(b).

As described above, there is a case where a blood pressure descending state remains unchanged even if the heart is paced with the pacemaker. Therefore, it is very important to measure a blood pressure of the patient with the pacemaker attached. For those reasons, the patient monitoring apparatus, by convention, detects an abrupt change of blood pressure through the monitoring of heat rates, and generates an alarm. The operator recognizes the alarm and manually operates the NIBP to measure a blood pressure of the patient attached with pacemaker.

An optimum range of heart rates set for generating an alarm is different for each patient, and therefore its setting is complicated. When a bradycardia occurs in the patient, the pacing of the heart is immediately started. Therefore, the heat-rate basis alarm is not always generated.

For the patient attached with a pacemaker, an immediate monitoring of his blood pressure is essential when a bradycardia occurs. In this case, the operator drives the NIBP by manual after the alarm generation, and this makes it difficult for the operator to quickly start the blood pressure measurement.

SUMMARY OF THE INVENTION

Accordingly, an object of the present invention is to measure a blood pressure of a patient attached with a pacemaker at a proper timing by use of a non-invasive blood-pressure measuring apparatus (NIBP).

To achieve the above object, there is provided a patient monitoring apparatus for monitoring at least electrocardiograms led from an electrocardiogram electrode, the apparatus comprising: mode-status judging means for judging that patient is in the pacing mode, and informing means for informing an operator of a mode status detected by the mode-status judging means.

With such an arrangement, when the pacing of the heart by the pacemaker is surely performed, the informing means informs the operator of the heart being paced.

According to another aspect of the invention, there is provided a patient monitoring apparatus for monitoring at least electrocardiograms led from an electrocardiogram electrode and blood pressure information output from a non-invasive blood-pressure measuring apparatus, the apparatus comprising: pacing-pulse detecting means for detecting pacing pulses caused by a pacemaker by use of the electrocardiogram; and first blood-pressure initiate means for intiating up the non-invasive blood-pressure measuring apparatus in response to a pacing pulse output from the pacing-pulse detecting means.

In the thus constructed patient monitoring apparatus, the non-invasive blood-pressure measuring apparatus is automatically operated when the pacemaker starts its pacing operation.

According to still another aspect of the present invention, there is provided a patient monitoring apparatus for monitoring at least electrocardiograms led from an electrocardiogram electrode and blood pressure information output from a non-invasive blood-pressure measuring apparatus, the apparatus comprising: mode-status judging means for judging that the patient is in the pacing mode; and second blood-pressure initiate means initiating the non-invasive blood-pressure measuring apparatus at preset time intervals when the mode-status judging means judges that the patient is in the pacing mode.

When a pacing mode is detected, the non-invasive blood-pressure measuring apparatus is initiated at preset time intervals during the pacing mode.

According to an additional aspect of the invention, there is provided a patient monitoring apparatus for monitoring at least electrocardiograms led from an electrocardiogram electrode and blood pressure information output from a non-invasive blood-pressure measuring apparatus, the apparatus comprising: pacing imcompetence judging means for judging whether or not the pacing by a pacemaker is imcompetence, on the basis of the electrocardiogram; and third blood-pressure initiate means for initiating the non-invasive blood-pressure measuring apparatus when the pacing imcompetence judging means judges that the pacing is imcompetence.

When the pacing is imcompetence, the pacing imcompetence is detected and the non-invasive blood-pressure measuring apparatus is initiated upon its detection.

According to a further aspect of the invention, there is provided a patient monitoring apparatus for monitoring at least electrocardiograms led from an electrocardiogram electrode and blood pressure information output from a non-invasive blood-pressure measuring apparatus, the apparatus comprising: mode-status judging means for judging that the patient is in a pacing mode; pacing imcompetence judging means for judging whether or not the pacing by a pacemaker is imcompetence, on the basis of the electrocardiogram; and fourth blood-pressure initiate means for initiating the non-invasive blood-pressure measuring apparatus at preset time intervals when the mode-status judging means judges that the patient is in the pacing mode, and for immediately initiating the non-invasive blood-pressure measuring apparatus when the pacing imcompetence judging means judges that the pacing is imperfect.

When a pacing mode is detected, the non-invasive blood-pressure measuring apparatus is initiated at preset time intervals during the pacing mode. Also when the pacing is imperfect, the non-invasive blood-pressure measuring apparatus is initiated.

BRIEF DESCRIPTION OF THE DRAWINGS

FIGS. 4 (A) to (F) are timing charts showing the operation of apparatus shown in FIG. 1;

FIGS. 14 (A) and (X)–(Y) are timing chart showing the apparatus shown in FIG. 11;

FIGS. 15 (A), (F), (X) and (Z) are timing chart showing an operation of the fifth embodiment;

FIGS. 16 (A)–(B) are waveform diagrams showing an electrocardiogram and a waveform representing an arterial blood pressure when the pacing progresses when the ventricle of the heart is paced and a dynamic state of the heart shifts from a sinus rhythm contraction to a phase of ventricular contraction;

DETAILED DESCRIPTION OF THE PREFERRED EMBODIMENTS

First Embodiment

Figure 1:
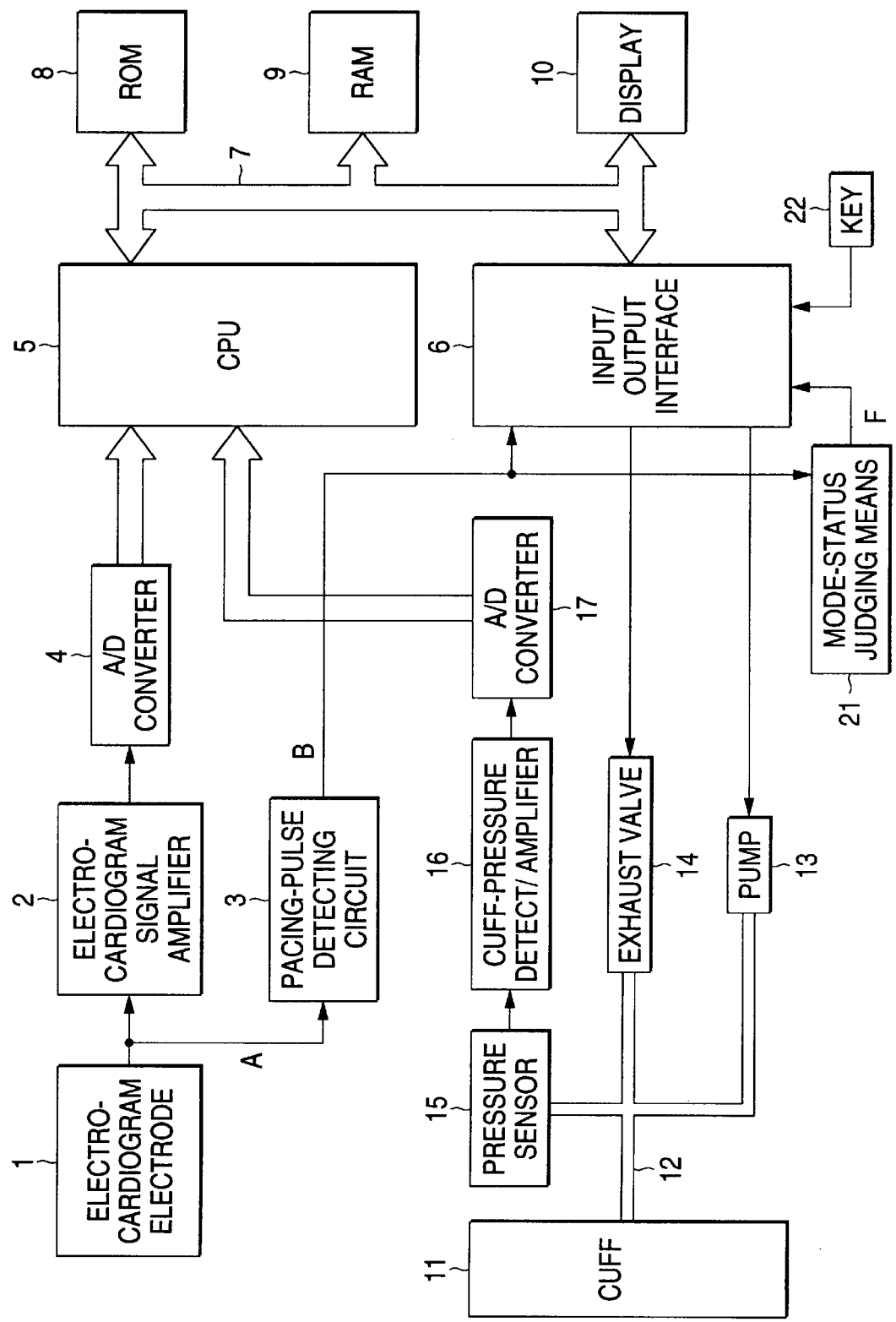
FIG. 1 is a block diagram showing an overall arrangement of a patient monitoring apparatus which is a first embodiment of the present invention.
Figure 2:
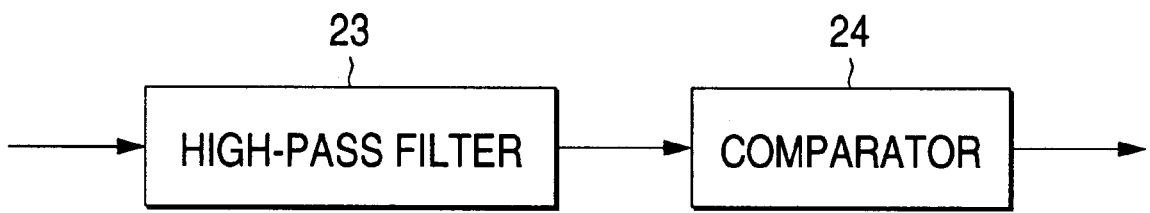
FIG. 2 is a block diagram showing a specific arrangement of a pacing-pulse detecting circuit 3 used in shown in FIG. 1.

FIG. 1 is a block diagram showing an overall arrangement of a patient monitoring apparatus which is a first embodiment of the present invention. An electrocardiogram electrode 1 is attached to the chest of a patient to pick up an electrocardiogram signal. An electrocardiogram signal led from the electrocardiogram electrode 1 is led to an amplifier 2 and a pacing-pulse detecting circuit 3. The amplifier 2 amplifies the electrocardiogram signal from the electrocardiogram electrode. The pacing-pulse detecting circuit 3 receives the electrocardiogram signal from the electrocardiogram electrode 1, and extracts a pacing signal from the received electrocardiogram signal. The detail of the pacing-pulse detecting circuit 3 is illustrated in FIG. 2. As shown, it includes a high-pass filter 23 and a comparator 24. The high-pass filter 23 permits high frequency components of the electrocardiogram signal to pass therethrough. The comparator 24 compares the amplitude of a signal output from the high-pass filter 23 with a preset value of amplitude, and produces a signal representative of the result of the amplitude comparison.

An output signal of the amplifier 2 for electrocardiogram signals is converted into a corresponding digital signal by an A/D convertor 4, and input to a CPU (central processing unit) 5. A signal representative of the result of the pacing signal detection, output from the pacing-pulse detecting circuit 3, is guided to an input/output interface 6.

A cuff 11 is wound around the arm of the patient. Air is forcibly supplied to the cuff 11, so that the patient's arm is pressurized with the cuff. The cuff 11 is coupled with a pump 13, an exhaust valve 14 and a pressure sensor 15 by way of a pipe 12. A signal representative of a pressure sensed by the pressure sensor 15 is applied to a cuff-pressure detect/amplifier unit 16. The pressure signal is detected and amplified by the cuff-pressure detect/amplifier unit 16; converted into a corresponding digital signal by an A/D convertor 17; and input to the CPU 5.

The CPU 5 controls the overall system of the patient monitoring apparatus. The CPU 5 is coupled with a ROM 8, a RAM 9, a display device 10 and the input/output interface 6, through a bus 7. Data and programs, used by the CPU 5, are stored in the ROM 8. In the course of the processings carried out by the CPU 5, data is temporarily stored and read out therefrom by the CPU 5.

The input/output interface 6 provides signal interfaces between the CPU 5 and its related portions. The input/output interface 6 is coupled for reception with the pacing-pulse detecting circuit 3. Control signals produced by the CPU 5 go to the pump 13 and the exhaust valve 14, through the input/output interface 6.

The non-invasive blood-pressure measuring apparatus (NIBP) of the present embodiment is of the known oscillometric type, and is made up of the cuff 11, pipe 12, pump 13, exhaust valve 14, pressure sensor 15, cuff-pressure detect/amplifier unit 16, input/output interface 6, A/D convertor 17, CPU 5, bus 7, ROM 8, RAM 9, and display device 10.

Figure 3:
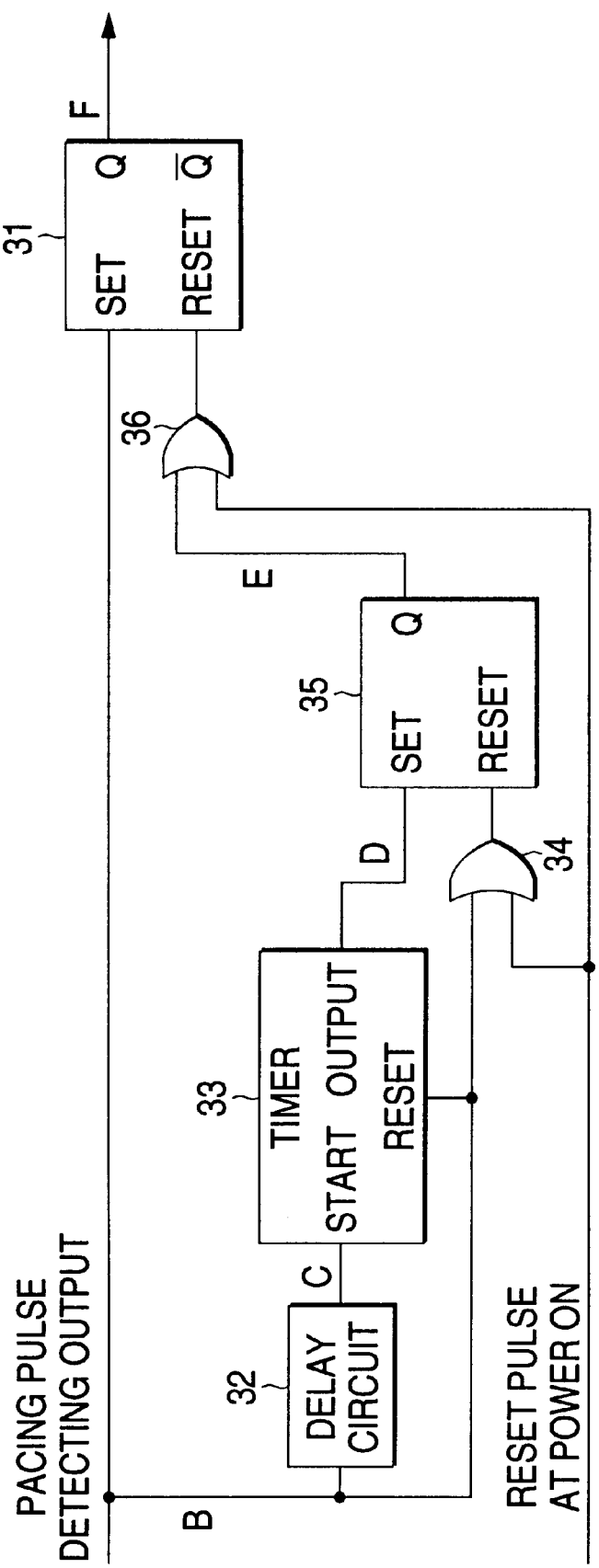
FIG. 3 is a circuit diagram showing the detail of a mode-status judging means 21 used in shown in FIG. 1.

A mode-status judging means 21 receives a pacing pulse from the pacing-pulse detecting circuit 3, and judges a mode status of the patient, a pacing mode or a nonpacing mode. In the pacing mode, the patient is paced with a pacemaker attached to him. The detail arrangement of the mode-status judging means 21 is shown in FIG. 3. In the figure, reference numeral 31 is a flip-flop; 32 is a delay circuit; 33 is a timer; 34 is an OR gate; 35 is a flip-flop; and 36 is an OR gate. A pacing signal coming from the pacing-pulse detecting circuit 3 is input to the set terminal of the flip-flop 31; is input to the start terminal of the timer 33 by way of the delay circuit 32; and input to the reset terminal of the timer 33; and is input to one of the input terminals of the OR gate 34. The output terminal of the timer 33 is connected to the set terminal of the flip-flop 35. The output terminal of the OR gate 34 is input to the reset terminal of the flip-flop 35. The Q terminal of the flip-flop 35 is connected to one of the input terminals of the OR gate 36. A reset pulse generated when the power switch (not shown) of the patient monitoring apparatus is turned on is applied to the other input terminals of the OR gates 34 and 36. The output terminal of the OR gate 36 is connected to the reset terminal of the flip-flop 31. An output signal output from the Q terminal of the flip-flop 31 is input to the input/output interface 6.

A key 22 (FIG. 1) is used when an operator instructs the NIBP to start a blood-pressure measurement. A signal generated when the key is operated reaches the CPU 5 through the input/output interface 6.

An operation of the patient monitoring apparatus thus arranged will be described with reference to a timing diagram shown in FIG. 4.

Upon power on, the flip-flops 31 and 35 are reset, and at this time an output signal F of low in logic level appears at the Q output terminal of the flip-flop 31. An electrocardiogram signal A that is led from the electrocardiogram electrode 1 reaches the pacing-pulse detecting circuit 3. At this time, if no pacing pulse by the pacemaker is not detected, no signal is input to the set terminal of the flip-flop 31. Because of this, the output signal F retains its low level at the Q output terminal of the flip-flop 31.

When the pacing-pulse detecting circuit 3 detects a pacing pulse, a pulse first appearing in an output signal (consisting of successive pacing pulses) B of the pacing-pulse detecting circuit 3 sets the flip-flop 31. The output signal F at the Q terminal of the flip-flop 31 goes high in logic level. The pacing-pulse detecting circuit 3 is reset by the first pulse of the output signal B of the pacing-pulse detecting circuit 3, and starts its operation in response to an output signal C of the delay circuit 32. The flip-flop 35 is reset by the first pacing pulse, and the output signal at its Q terminal goes low in logic level. When a succession of pacing pulses are detected, the timer 33 repeats its reset and start. A set time (one minute in this instance) of the timer 33 is much longer than the pacing interval. Therefore, an output signal D of the timer 33 remains low in logic level during the successive pacing operations. Therefore, an output signal E of the Q terminal of the flip-flop 35 is also low in logic level, and an output signal F is left high in logic level at the Q terminal of the flip-flop 31.

When no pacing pulse is detected by the pacing-pulse detecting circuit 3, the timer 33 started to count the successive pacing pulses from the last pulse thereof, and when the set time is reached, a pulse appears in the output signal D of the timer 33. This pulse sets the flip-flop 35 to render the output signal E (at the Q terminal of the flip-flop 35) high in logic level. The flip-flop 31 is reset, so that the output signal F at its Q terminal goes low.

Thus, the output signal F (appearing at the Q terminal of the flip-flop 31) goes high when a pacing mode is set up, while it goes low when the pacing mode is not set up. In other words, the output signal F represents a mode status.

The output signal F is input to the CPU 5, through the input/output interface 6. The CPU 5 interprets this mode status signal F, and if the signal represents a pacing mode, it causes the display device 10 to display the present mode status, or the pacing mode being set up. A doctor or nurse sees a message of the pacing mode being set up, and operates the key 22 to cause the NIBP to start a measurement of blood pressure.

The CPU 5 drive the pump 13 to supply air to the cuff 11 up to a predetermined pressure therein, and then opens the exhaust valve 14 to gradually decrease the pressure in the cuff 11. During this pressure descending period, the CPU 5 receives pressure data from the A/D convertor 17, and performs a blood-pressure measurement in a normal oscillometric manner, and drives the display device 10 to display the measurement result.

In the above-described embodiment, the circuit for detecting the pacing pulse signal consists of the combination of the filter and comparator. Alternatively, the CPU 5 receives the electrocardiogram signal and processes it to detect the pacing pulse signal.

Also in the embodiment, the display device 10 visually presents the pacing mode being set up. The same information may be presented acoustically or optically instead of the visual presentation. In other words, any means may be used if it is capable of informing the pacing mode being set up.

The hardware construction, i.e., the mode-status judging means 21 consisting of flip-flops, timers and others, is used for the mode detection. A software means may be used in place of the hardware means. In this case, the software means is executed by the CPU 5: a mode detection program is stored in the ROM 8, and the CPU 5 processes the output signal from the pacing-pulse detecting circuit 3 under control of the program read out of the ROM.

In the first embodiment, the CPU 5 performs a normal patient monitoring operation. That is, the CPU 5 processes the output signal of the amplifier 2 and causes the display device 10 to display an electrocardiogram.

Second Embodiment

Figure 5:
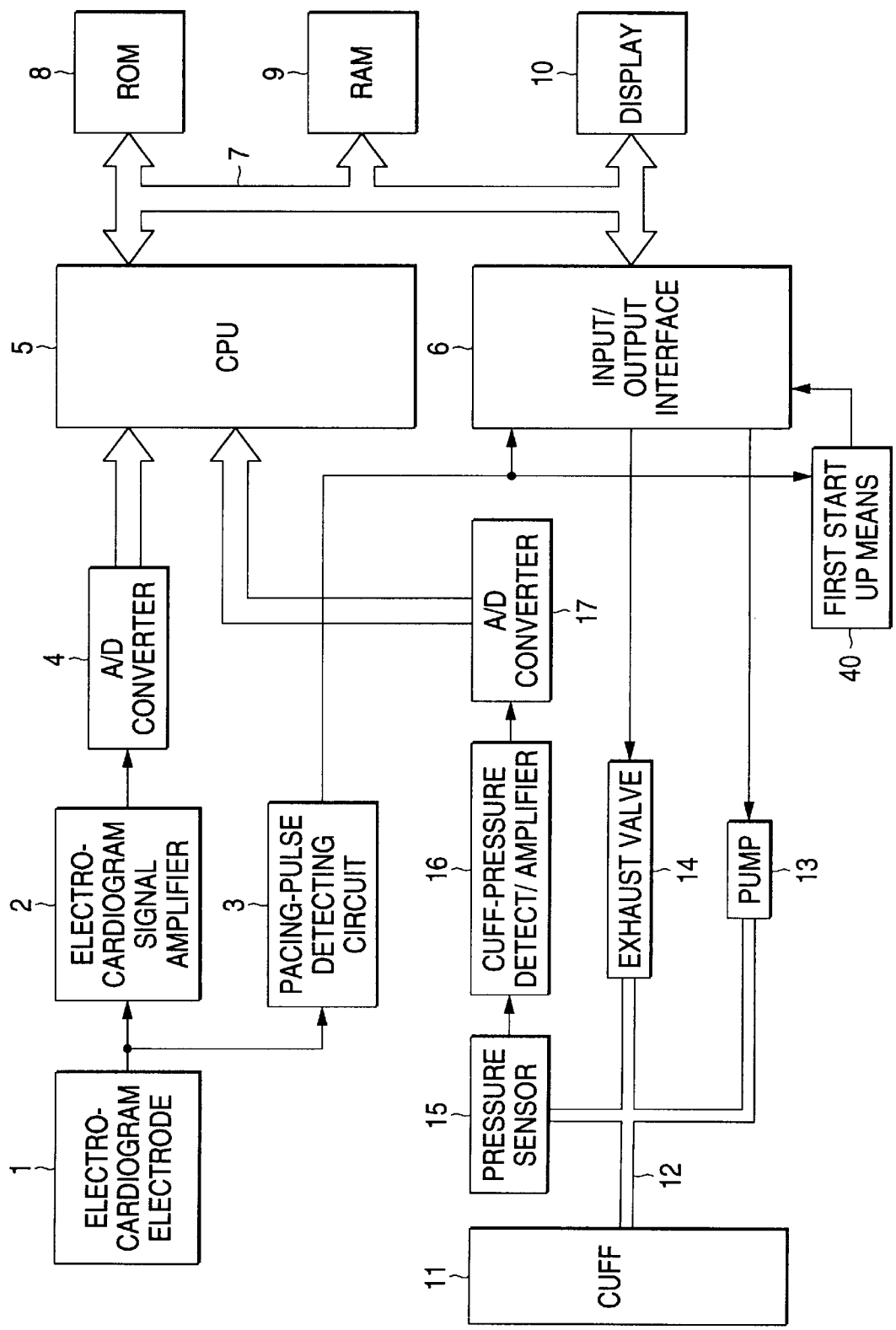
FIG. 5 is a block diagram showing an overall arrangement of a patient monitoring apparatus which is a second embodiment of the present invention.

A second embodiment of the present invention will be described. An overall arrangement of the second embodiment is shown in FIG. 5. The second embodiment uses a first initiate means 40 in place of the mode-status judging means 21 and the key 22, which are used in the first embodiment.

Figure 6:
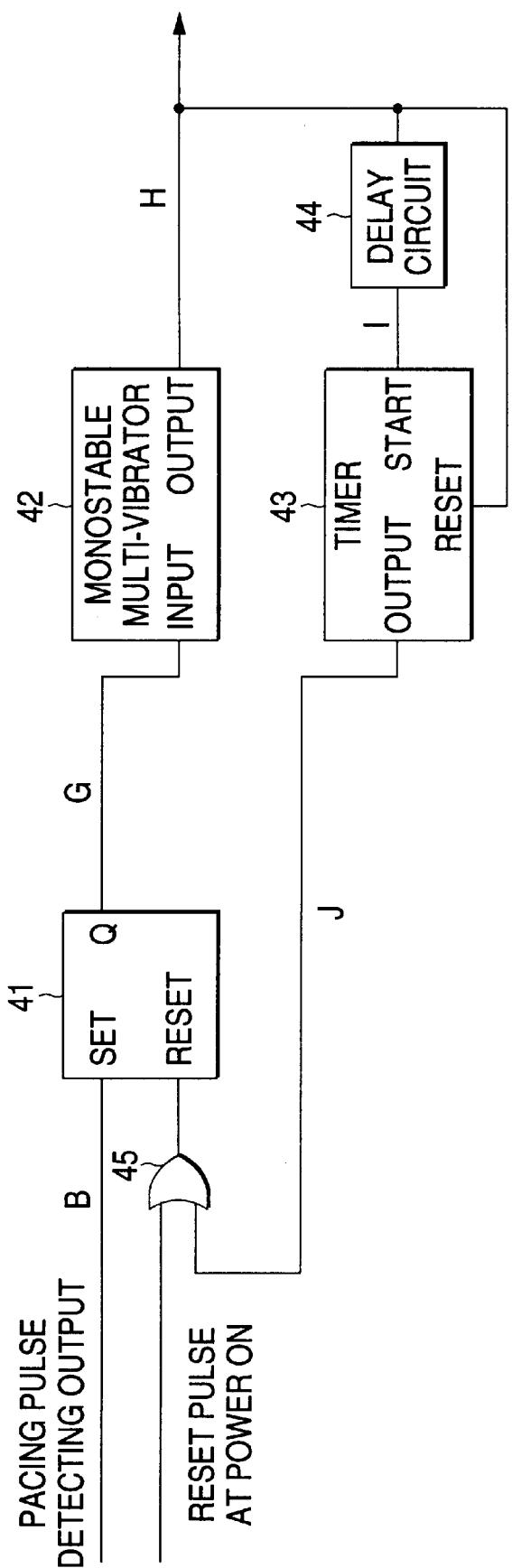
FIG. 6 is a circuit diagram showing the detail of a first initiate means 40 used in the apparatus shown in FIG. 5.
Figure 7A:
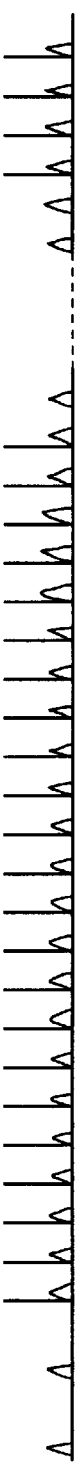
FIGS. 7 (A), (B) and (G)–(K) are timing chart showing an operation of the apparatus shown in FIG. 5.
Figure 7B:
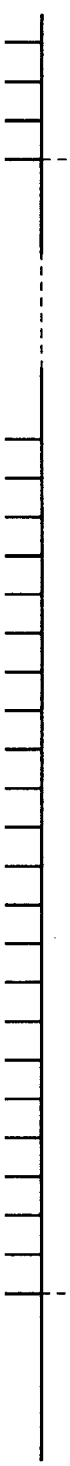
Figure 7G:
Figure 7H:
Figure 7I:
Figure 7J:
Figure 7K:

The first initiate means 40, which is essential to the second embodiment, is arranged as shown in FIG. 6. In the figure, reference numeral 41 is a flip-flop; 42 is a monostable multi-vibrator; 43 is a timer; 44 is a delay circuit; and 45 is an OR gate. As shown, the set terminal of the flip-flop 41 is connected for reception to a detect signal B from the pacing-pulse detecting circuit 3. The Q terminal of the flip-flop 41 is connected to the input terminal of the monostable multi-vibrator 42. An output signal H of the monostable multi-vibrator 42 is connected to the input/output interface 6 and the reset terminal of the timer 43. The output signal H is also connected to the start terminal of the timer 43, through the delay circuit 44. The output terminal of the timer 43 is connected to a first terminal of the OR gate 45. The output terminal of the OR gate 45 is connected to the reset terminal of the flip-flop 41. A reset pulse signal, generated at the time of power on, is applied to a second input terminal of the OR gate 45.

Like reference numerals are used to designate the same components of the remaining ones as of the first embodiment, and no further description of them will be given. In the second embodiment, programs stored in the ROM 8 and to be used for the processings by the CPU 5 are somewhat different from those of the first embodiment.

An operation of the thus arranged patient monitoring apparatus will be described with reference to a timing chart of FIG. 7. Upon power on, the flip-flop 41 is reset, and a signal of low in logic level appears at the Q terminal of the flip-flop 41. An electrocardiogram signal A led from the electrocardiogram electrode 1 reaches the pacing-pulse detecting circuit 3. When the pacing-pulse detecting circuit 3 detects no pacing pulse signal, no signal is input to the set terminal of the flip-flop 41. Therefore, the output signal G remains low in logic level at the Q terminal of the flip-flop 41, and the output signal H of the monostable multi-vibrator 42 also remains low.

When the pacing-pulse detecting circuit 3 detects a pacing pulse, a first pulse of a train of pulses of the detect signal B of the pacing-pulse detecting circuit 3 sets the flip-flop 41. In turn, the output signal at the Q terminal of the flip-flop 41 goes high. As a result, one pulse appears in the output signal H of the monostable multi-vibrator 42. In response to this pulse, the CPU 5 drives the non-invasive blood-pressure measuring apparatus (NIBP) to start a blood pressure measurement. The blood pressure measurement is performed as in the first embodiment.

The timer 43 starts to count time in response to a pulse of the output signal I from the delay circuit 44, after it is reset by the above-mentioned pulse output from the monostable multi-vibrator 42. After power on, the flip-flop 41 is not reset till a pulse of the output signal J of the timer 43. It never happens that the non-invasive blood-pressure measuring apparatus starts the blood pressure measure again immediately after the ending of the blood pressure measurement by the apparatus, so long as the pacing pulses are successively detected (wave K in FIG. 7). When the set time duration terminates and a pulse indicative of it appears in the output signal J of the timer 43, the flip-flop 41 is reset, and set by a pacing pulse thereafter applied to the set terminal of the flip-flop. Therefore, a pulse appears in the output signal H of the monostable multi-vibrator 42. In response to this pulse, the CPU 5 causes the NIBP to start a blood pressure measurement, and the timer 43 is reset and starts to count time. The NIBP repeats the blood pressure measurement at fixed time intervals in a similar manner so long as the pacing pulses are successively detected.

When the pacing pulse stops, the flip-flop 41 has been reset by the timer 43, but it is not set, no pulse appears in the output signal H of the monostable multi-vibrator 42, and the blood pressure measurement is not carried out by the NIBP. When the pacing pulse appears again, the flip-flop 41 is set, a pulse appears in the output signal H of the monostable multi-vibrator 42, and the blood pressure measurement is carried out.

Subsequently, the blood pressure measurement is carried out in a similar way. Thus, in the second embodiment, the patient monitoring apparatus under discussion is designed such that the next blood pressure measurement does not start till a preset time (preferably 2.5 to 5 minutes) elapses from the end of one blood pressure measurement. Therefore, if the pacing pulse is successively detected, the blood pressure measurement is carried out at the preset time intervals. There is no chance of excessively pressurizing the arm of the patient by the cuff.

In the second embodiment mentioned above, the hardware construction including the flip-flops, monostable multi-vibrator and others is used for constructing the first initiate means 40. The first initiate means 40 may be constructed by the software technique, as a matter of course.

Third Embodiment

Figure 8:
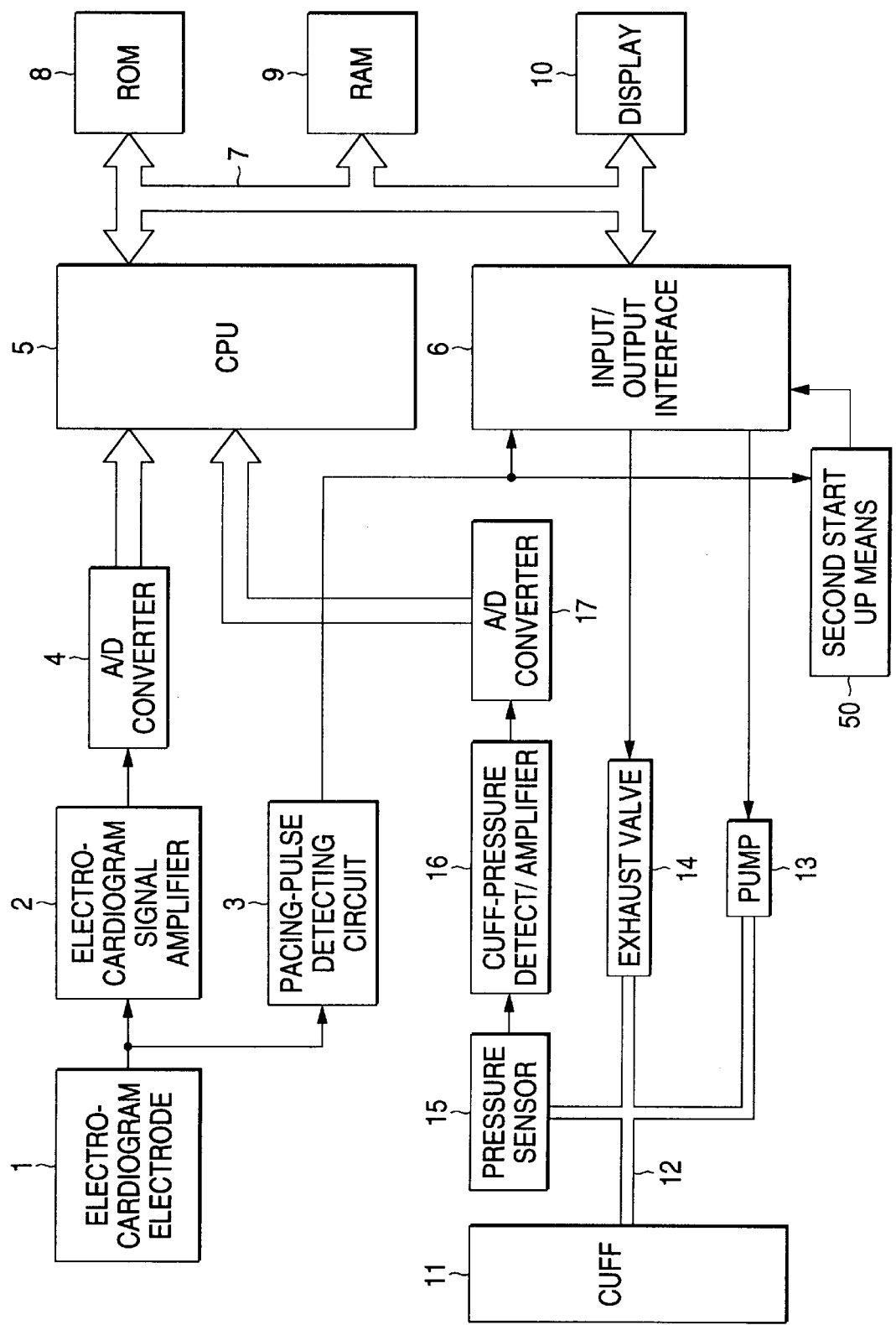
FIG. 8 is a block diagram showing an overall arrangement of a patient monitoring apparatus which is a third embodiment of the present invention.

A third embodiment of the present invention will be described. An overall arrangement of a patient monitoring apparatus constituting the third embodiment is illustrated in FIG. 8. The third embodiment uses a second initiate means 50 in place of the first initiate means 40, which is used in the second embodiment.

Figure 9:
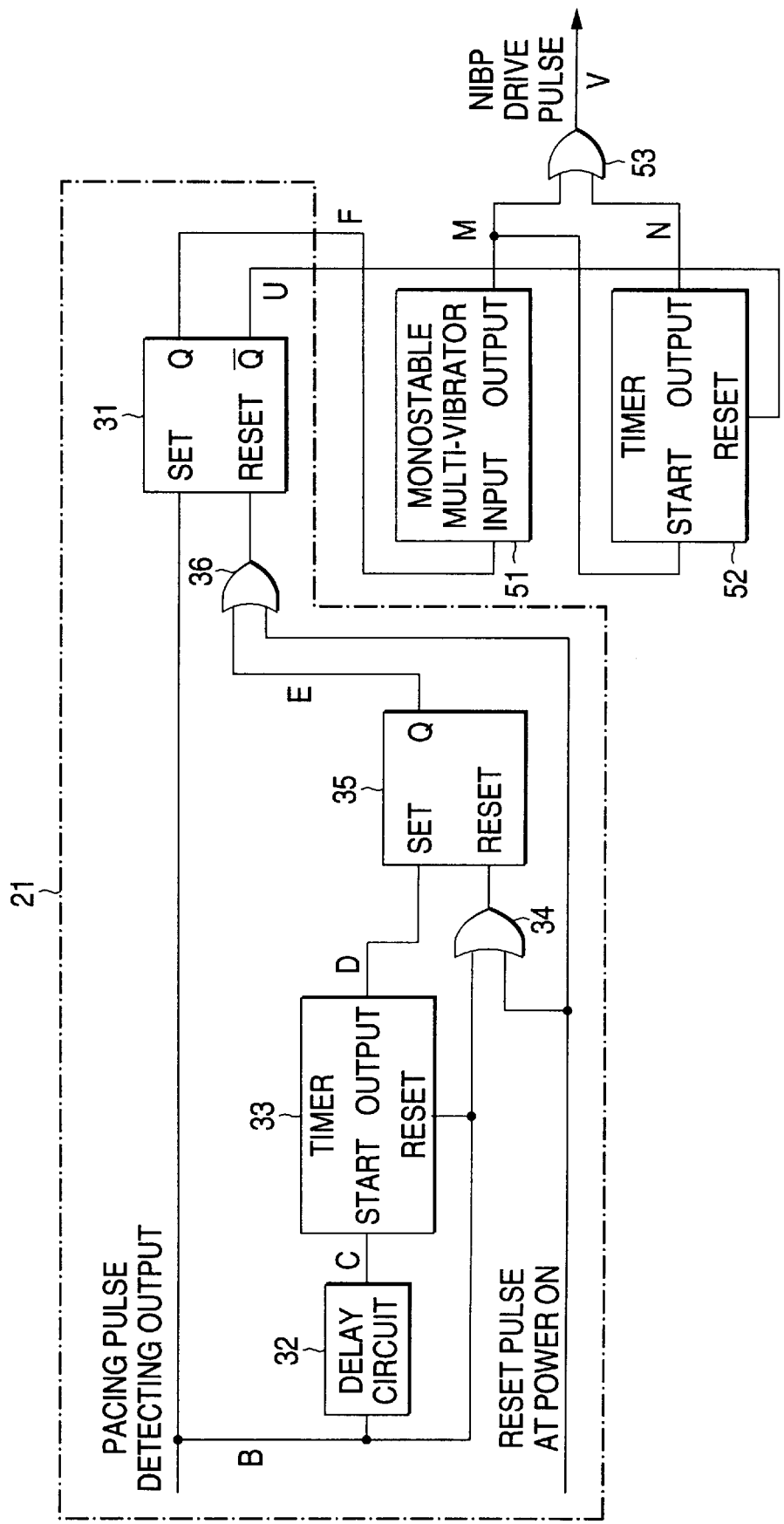
FIG. 9 is a circuit diagram showing the detail of a second initiate means 50 used in the FIG. 8 apparatus.

The detailed arrangement of the second initiate means 50 is illustrated in FIG. 9. In the figure, reference numeral 31 is a flip-flop; 32 is a delay circuit; 33 is a timer; 34 is an OR gate; 35 is a flip-flop; 36 is an OR gate; 51 is a monostable multi-vibrator; 52 is a timer; 53 is an OR gate. As shown, the second initiate means 50 is made up of the mode-status judging means 21, a monostable multi-vibrator 51, timer 52 and an OR gate 53. The mode-status judging means 21 is the same as the mode-status judging means 21 in the first embodiment, and hence description thereof is omitted. The Q terminal of the flip-flop 31 in the mode-status judging means 21 is connected to the input terminal of the monostable multi-vibrator 51. The inverted Q terminal of the flip-flop 31 is connected to the reset terminal of the timer 52. The output terminal of the monostable multi-vibrator 51 is connected to a first input terminal of the OR gate 53 and a start terminal of the timer 52. The output terminal of the timer 52 is connected to a second input terminal of the OR gate 53. An output signal of the OR gate 53 is connected to the input/output interface 6.

Like reference numerals are used to designate the same components of the remaining ones as of the second embodiment, and no further description of them will be given.

Figure 10:
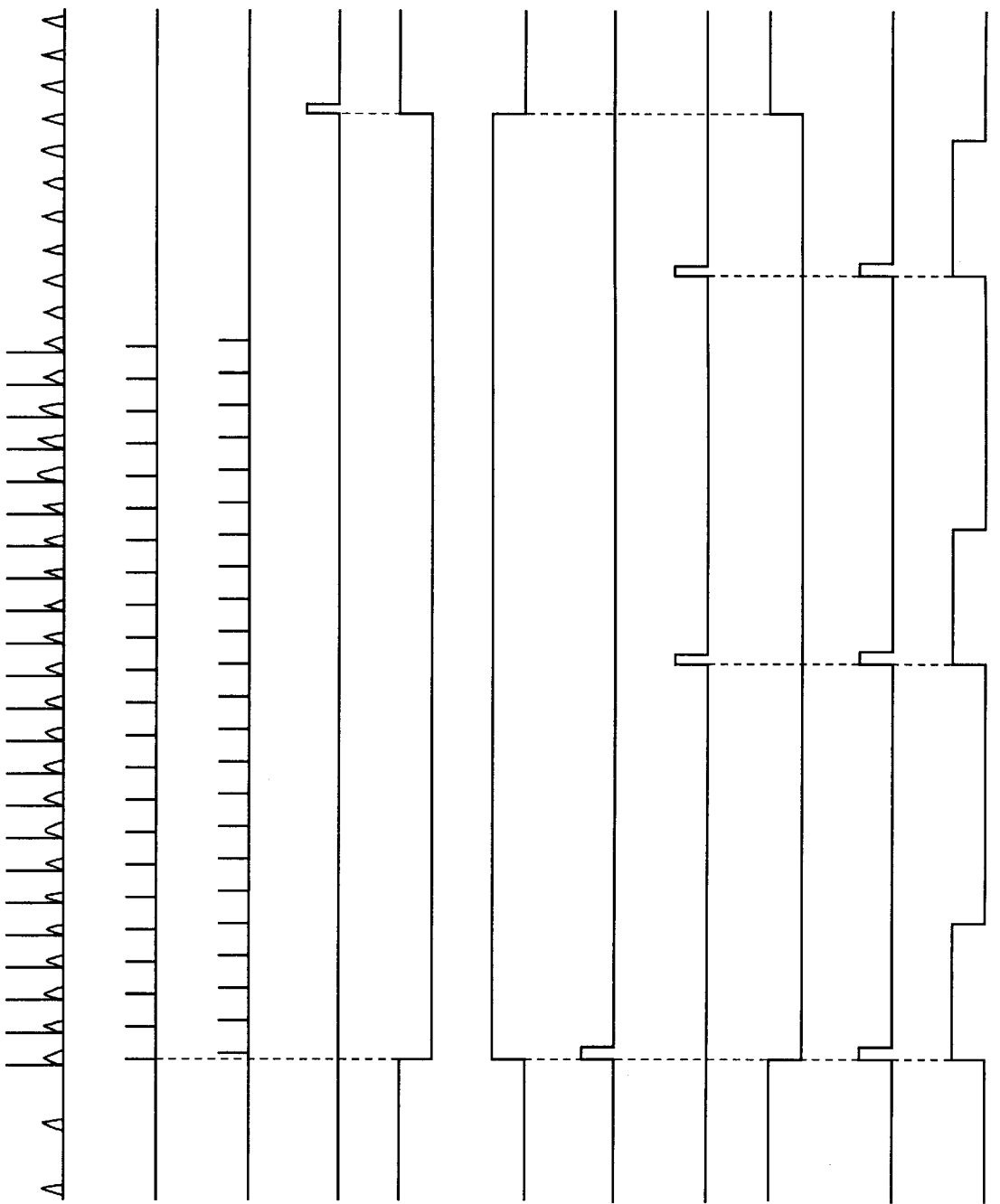
FIGS. 10 (A)–(F),(M)–(N) and (U)–(W) are timing charts showing an operation of the apparatus shown in FIG. 8.

An operation of the thus arranged patient monitoring apparatus will be described with reference to a timing chart of FIG. 10.

As in the first embodiment, the mode-status judging means 21, after power on, renders the output signal F at the Q terminal of the flip-flop 31 high or low in logic level in accordance with a state of the pacing pulse that is extracted from the electrocardiogram by the pacing-pulse detecting circuit 3. In other words, the mode-status judging means 21 detects a mode status, a pacing mode or a nonpacing mode of the patient monitoring apparatus. An output terminal from the inverted Q terminal of the flip-flop 31 serves as a reset signal to the timer 52.

When the made status of the patient shifts it from a nonpacing mode to a pacing mode, one pulse appears in the output signal M of the monostable multi-vibrator 51. This pulse starts the timer 52 to operate and is transmitted to the CPU 5 by way of the OR gate 53 and the input/output interface 6. That is, a drive pulse appears in the output signal V of the OR gate 53. In response to this pulse, the CPU 5 causes the non-invasive blood-pressure measuring apparatus (NIBP) to start its blood pressure measuring operation. The blood pressure measuring method is the same as in the first and second embodiments. In the pacing mode, the timer 52 repeats its time counting operation, and pulses appear at given time intervals (2.5 to 5 minutes) in the output signal N of the timer 52. Those pulses, like the pulses appearing in the output signal M of the monostable multi-vibrator 51, are transmitted to the CPU 5 in the form of the drive pulses of the NIBP. With those pulses, the NIBP performs the blood pressure measurement at preset time intervals.

When the made status of the patient changes it from the pacing mode to the nonpacing mode, the timer 52 is reset to inhibit the timer 52 and the monostable multi-vibrator 51 from producing drive pulses. Therefore, no blood pressure measurement is carried out by the NIBP. The non-invasive blood-pressure measuring apparatus operates as indicated by a waveform W in FIG. 10.

As described above, in the patient monitoring apparatus, the second initiate means checks a mode status of the patient, a pacing mode or a nonpacing mode. In the pacing mode, the blood pressure measurement is performed, while in the nonpacing mode, it is not performed. The useful effects of the this embodiment are comparable with those of the second embodiment.

In the third embodiment mentioned above, the hardware construction including the flip-flops, monostable multivibrator and others is used for constructing the second initiate means 50. The second initiate means 50 may be constructed by the software technique, as a matter of course.

Fourth Embodiment

Figure 11:
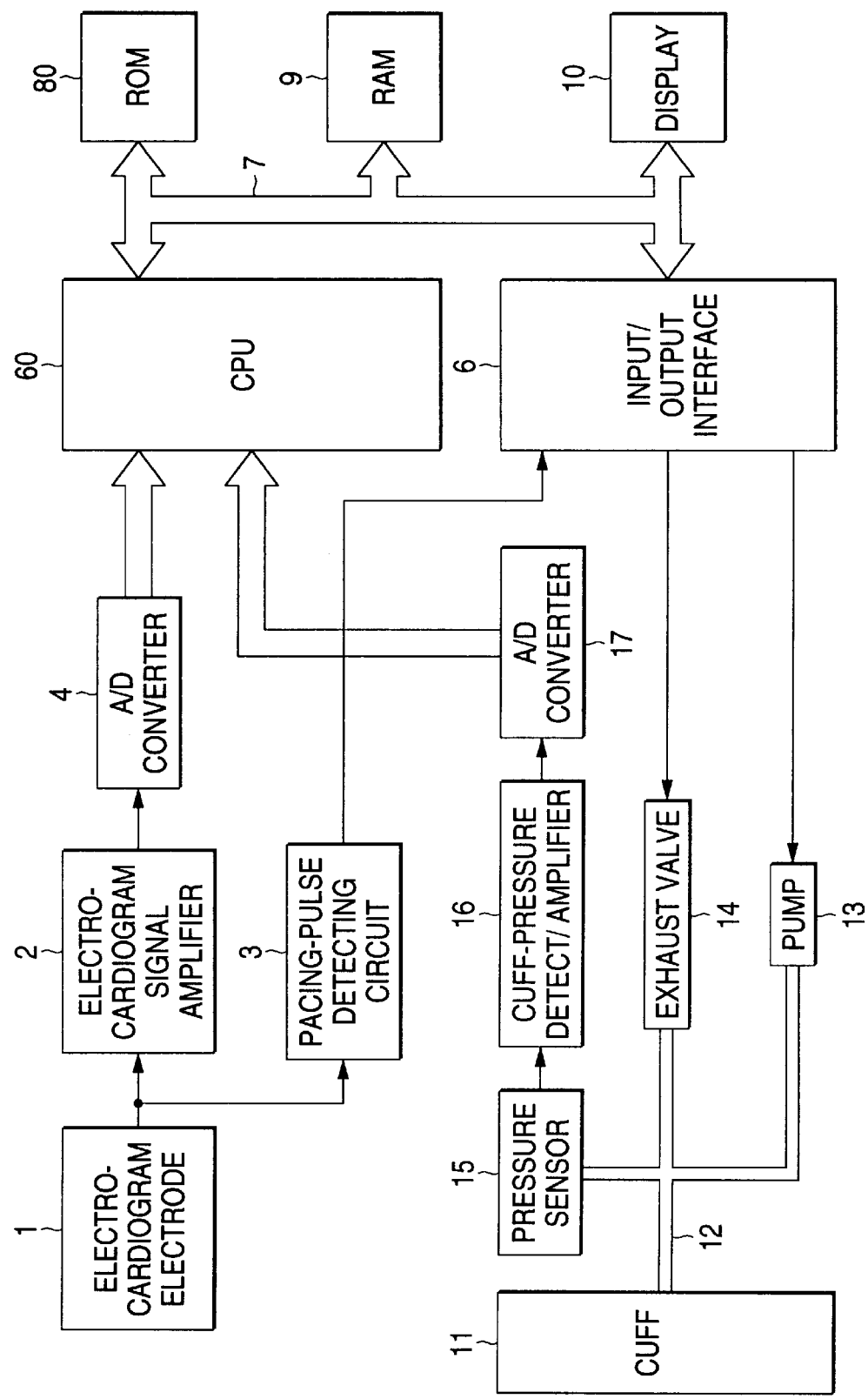
FIG. 11 is a block diagram showing an overall arrangement of a patient monitoring apparatus which is a fourth embodiment of the present invention.

A fourth embodiment of the present invention will be described. An overall arrangement of a patient monitoring apparatus constituting the fourth embodiment is illustrated in FIG. 11. The fourth embodiment is equivalent to the third embodiment not including the second initiate means 50. In the fourth embodiment, a program that is stored in a ROM 80 and executed by a CPU 60 is different from that in the third embodiment. The CPU 60 has the functions of respective means shown in FIG. 12.

Like reference numerals are used to designate the same components of the remaining ones as of the third embodiment, and no further description of them will be given.

Figure 12:
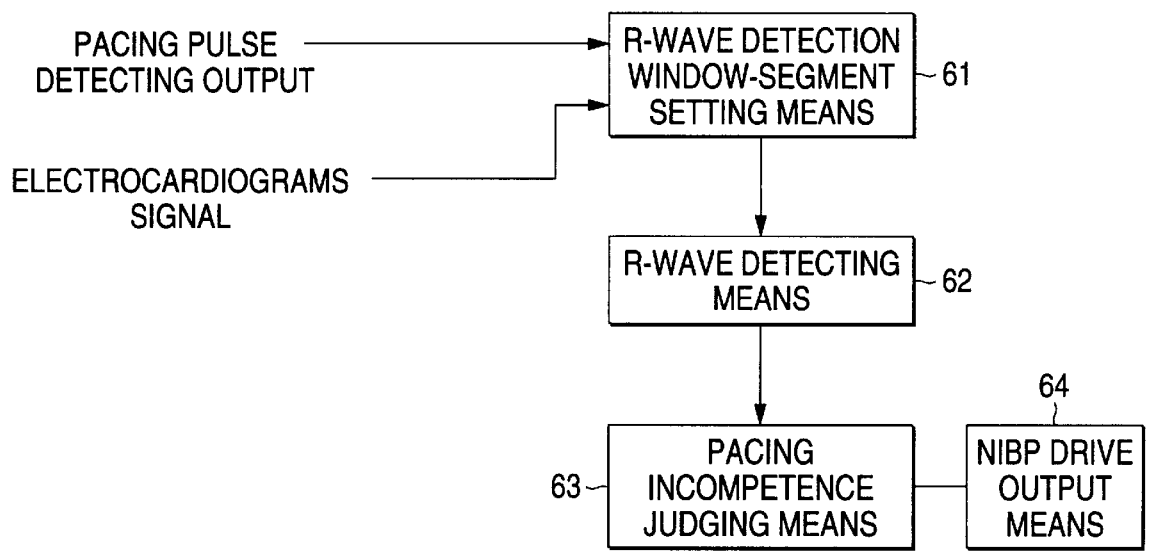
FIG. 12 is a flow chart showing an operation of the apparatus shown in FIG. 11.

An operation of the thus arranged patient monitoring apparatus will be described with reference to a functional block diagram of FIG. 12.

Figure 13:
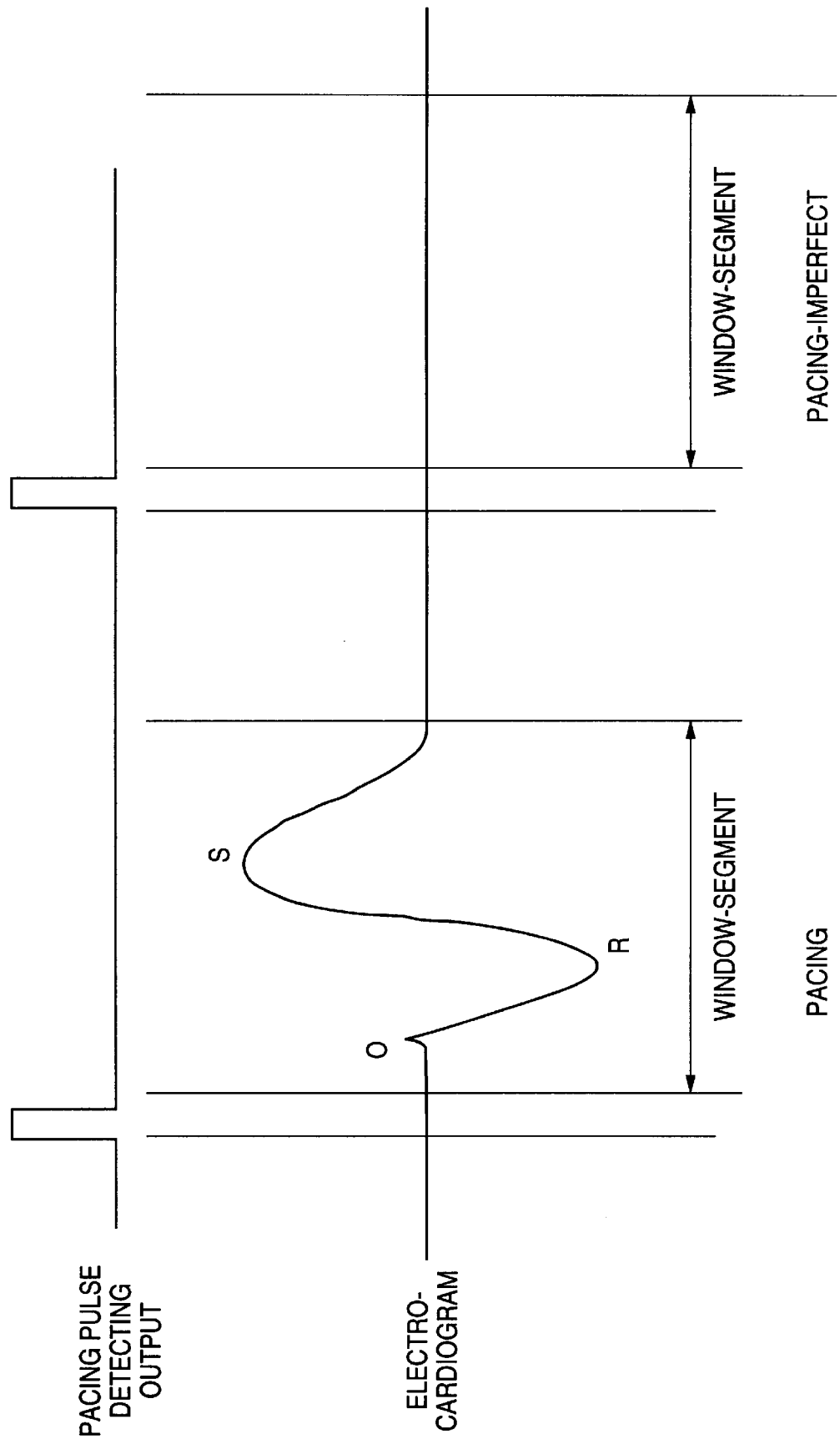
FIG. 13 is a waveform diagram showing an operation of the apparatus shown in FIG. 11.
Figures 17A, 17B:
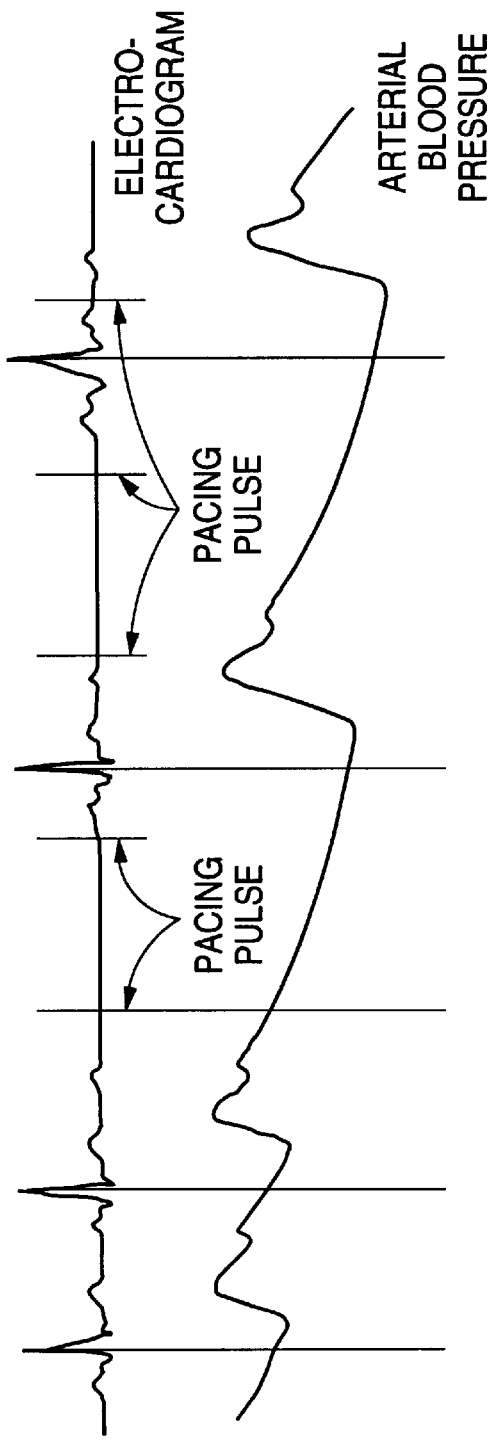
FIGS. 17 (A)–(B) are waveform diagrams showing an electrocardiogram and a waveform representing an arterial blood pressure when the pacing progresses when the pacing becomes imperfect in spite pacing to recover from a bradycardia.

Reference numerals and their names in FIG. 12 will first be described: numeral 61 is R-wave detection window-segment setting means; 62 is R-wave detecting means; 63 is pacing imcompetence judging means; and 64 is NIBP drive pulse output means. The R-wave detection window-segment setting means 61 receives a pacing-pulse detect output signal from the pacing-pulse detecting circuit 3 and an electrocardiogram signal from the electrocardiogram electrode 1, and sets a window segment by use of those received signals as shown in FIG. 13. The window segment is preferably any of 15 to 150 msec after the pacing pulse is detected. The R-wave detecting means 62 detects an R wave. The R-wave caused by the pacing takes the form of a left bundle branch block (LBBB), and a pattern matching technique is used for the detection of the R-wave. The pacing imcompetence judging means 63 judges whether or not the pacing is imcompetence on the basis of the result of the R-wave detection by the pattern matching. If the pacing is imcompetence, the NIBP drive pulse output means 64 generates drive pulses to drive the non-invasive blood-pressure measuring apparatus to start its blood pressure measurement. FIG. 14 shows a timing chart of an electrocardiogram signal (A), drive pulses (X) of the non-invasive blood-pressure measuring apparatus and an operation state (Y) of the non-invasive blood-pressure measuring apparatus. After driving the non-invasive blood-pressure measuring apparatus, the blood pressure measurement is not affected by the drive pulses that will recur till the measurement ends.

In the present embodiment, when the pacing imcompetence is detected, the non-invasive blood-pressure measuring apparatus is immediately driven to start its blood pressure measurement. If necessary, the pacing imcompetence may be presented to the operator in a suitable manner.

Fifth Embodiment

A fifth embodiment of the present invention will be described. This embodiment incorporates the combination of the functions of the CPU 5 in the third embodiment and the functions of the CPU 60 in the fourth embodiment.

In the fifth embodiment, as shown in FIG. 15, a drive pulse X to drive the non-invasive blood-pressure measuring apparatus are generated when a pacing mode is set up. When the pacing mode subsequently continues, the drive pulses are generated at preset time intervals. The same is generated also when the pacing is imcompetence. In response to the drive pulse, the non-invasive blood-pressure measuring apparatus is started up. An operation state of the non-invasive blood-pressure measuring apparatus is depicted as a waveform Z.

In the patient monitoring apparatus of the present invention, when the pacing of the heart by the pacemaker is performed, the informing means informs the operator of the heart being paced. The operator can know a proper timing to initiate the non-invasive blood-pressure measuring apparatus from the information presented by the informing means.

In the apparatus of the present invention, the non-invasive blood-pressure measuring apparatus is driven upon the detection of a pacing pulse. The pacing pulses are generated by the pacemaker when a bradycardia occurs due to a sinus block or an atrioventricular block. The timing of the generation of the pacing pulse is coincident with the timing of initiating or driving the non-invasive blood-pressure measuring apparatus. Therefore, there is no need of providing a means to get the drive timing. The conventional apparatus monitors the heat rate and detects a bradycardia on the basis of the heat rate. The apparatus of the invention eliminates the use of the functioning means. As described above, the means for monitoring the heat rate needs the work of setting an optimum range of the heart rates different for each patient. The apparatus of the invention eliminates such a troublesome setting work, leading to labor saving.

In the conventional patient monitoring apparatus, when an alarm is generated, the operator manually operates the non-invasive blood-pressure measuring apparatus. On the other hand, the patient monitoring apparatus of the present invention automatically starts up the non-invasive blood-pressure measuring apparatus when the pacing pulse appears. Therefore, the non-invasive blood-pressure measuring apparatus may be started up quickly and at a proper timing.

In the patient monitoring apparatus of the present invention, when a pacing mode is detected, the non-invasive blood-pressure measuring apparatus is started up at preset time intervals during the pacing mode. Therefore, there is avoided a continuous measurement of blood pressure, and hence there is no chance of excessively pressurizing the arm of the patient by the cuff.

In the patient monitoring apparatus of the present invention, when the pacing is imcompetence, the pacing imcompetence is detected and the non-invasive blood-pressure measuring apparatus is started up upon its detection.

In the patient monitoring apparatus of the present invention, the non-invasive blood pressure measurement is repeated at preset time intervals during the pacing mode. When a pacing imcompetence occurs during the pacing mode, the blood pressure measurement by the non-invasive blood-pressure measuring apparatus starts at that time. In other words, when the blood pressure measurement is most required, the blood pressure measurement is quickly started.

What is claimed is:

1. A patient monitoring apparatus for monitoring at least electrocardiograms led from an electrocardiogram electrode and blood pressure information output from a non-invasive blood-pressure measuring apparatus, comprising:

mode-status judging means for judging that said patient is in the pacing mode;

pacing imcompetence judging means for judging whether or not the pacing by a pacemaker is imcompetence, on the basis of said electrocardiogram; and fourth blood-pressure initiate means for initiating the non-invasive blood-pressure measuring apparatus at preset time intervals when said mode-status judging means judges that said patient is in the pacing mode, and for immediately initiating the non-invasive blood-pressure measuring apparatus when said pacing imcompetence judging means judges that the pacing is imcompetence.

* * * * *